(12) United States Patent
Greenberg et al.

(10) Patent No.: US 7,738,962 B2
(45) Date of Patent: Jun. 15, 2010

(54) FITTING OF BRIGHTNESS IN A VISUAL PROSTHESIS

(75) Inventors: Robert Jay Greenberg, Los Angeles, CA (US); Ione Fine, Del Mar, CA (US); Arup Roy, Valencia, CA (US); Matthew J. McMahon, Los Angeles, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 650 days.

(21) Appl. No.: 11/357,680

(22) Filed: Feb. 16, 2006

(65) Prior Publication Data

US 2006/0184062 A1 Aug. 17, 2006

Related U.S. Application Data

(60) Provisional application No. 60/653,674, filed on Feb. 16, 2005.

(51) Int. Cl.
*A61N 1/36* (2006.01)
*A61N 1/05* (2006.01)

(52) U.S. Cl. .......................................... 607/53; 607/54
(58) Field of Classification Search ................ 623/6.63; 607/50, 53, 54
See application file for complete search history.

(56) References Cited

U.S. PATENT DOCUMENTS

| | | | | |
|---|---|---|---|---|
| 4,628,933 A | * | 12/1986 | Michelson | 607/53 |
| 5,109,844 A | * | 5/1992 | de Juan et al. | 607/53 |
| 5,159,927 A | * | 11/1992 | Schmid | 607/53 |
| 5,575,813 A | | 11/1996 | Edell et al. | |
| 5,935,155 A | | 8/1999 | Humayun et al. | |
| 5,944,747 A | | 8/1999 | Greenberg et al. | |
| 6,374,143 B1 | | 4/2002 | Berrang et al. | |
| 6,400,989 B1 | | 6/2002 | Eckmiller | |
| 6,458,157 B1 | * | 10/2002 | Suaning | 623/6.63 |
| 6,516,228 B1 | | 2/2003 | Berrang et al. | |
| 6,843,870 B1 | | 1/2005 | Bluger | |
| 7,031,776 B2 | * | 4/2006 | Chow et al. | 607/54 |
| 7,308,315 B2 | * | 12/2007 | Ohta et al. | 607/54 |
| 7,321,795 B2 | * | 1/2008 | Bogdanowicz | 607/53 |
| 7,321,796 B2 | * | 1/2008 | Fink et al. | 607/54 |
| 2002/0091421 A1 | | 7/2002 | Greenberg et al. | |
| 2002/0111658 A1 | | 8/2002 | Greenberg et al. | |
| 2003/0181957 A1 | | 9/2003 | Greenberg et al. | |
| 2004/0236389 A1 | | 11/2004 | Fink et al. | |

FOREIGN PATENT DOCUMENTS

WO WO 00/56393 * 9/2000

* cited by examiner

*Primary Examiner*—Carl H Layno
*Assistant Examiner*—Luther G Behringer
(74) *Attorney, Agent, or Firm*—Scott B. Dunbar; Alessandro Steinfl

(57) ABSTRACT

The invention is a method of automatically adjusting an electrode array to the neural characteristics of an individual patient. The perceptual response to electrical neural stimulation varies from patient to patient and The response to electrical neural stimulation varies from patient to patient and the relationship between current and perceived brightness is often non-linear. It is necessary to determine this relationship to fit the prosthesis settings for each patient. It is advantageous to map the perceptual responses to stimuli. The method of mapping of the present invention is to provide a plurality of stimuli that vary in current, voltage, pulse duration, frequency, or some other dimension; measuring and recording the response to those stimuli; deriving a formula or equation describing the map from the individual points; storing the formula; and using that formula to map future stimulation.

24 Claims, 8 Drawing Sheets

FITTING OF BRIGHTNESS IN A VISUAL PROSTHESIS

CROSS REFERENCE TO RELATED APPLICATIONS

This application claims priority to U.S. Provisional Patent Application 60/653,674, filed Feb. 16, 2005, for A Method of Determining the Electrical Current Amplitude Required to Produce a Percept. This application is related to and incorporates herein by reference, U.S. patent application Ser. No. 10/864,590 filed Jun. 8, 2004 for Automatic Fitting for a Visual Prosthesis.

GOVERNMENT RIGHTS NOTICE

This invention was made with government support under grant No. R24EY12893-01, awarded by the National Institutes of Health. The government has certain rights in the invention.

FIELD OF THE INVENTION

The present invention is generally directed to neural stimulation and more specifically to an improved method of Optimizing neural stimulation levels for artificial vision.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparatuses to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretial). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

In addition to the electrode arrays described above, there are several methods of mapping a high resolution camera image to a lower resolution electrode array. U.S. Pat. No. 6,400,989 to Eckmiller describes spatio-temporal filters for controlling patterns of stimulation in an array of electrodes. The assignee of the present application has two related U.S. patent applications: Ser. No. 09/515,373, filed Feb. 29, 2000, entitled Retinal Color Prosthesis for Color Sight Restoration; and Ser. No. 09/851,268, filed May 7, 2001, entitled Method, Apparatus and System for Improved Electronic Acuity and Perceived Resolution Using Eye Jitter Like Motion. Both applications are incorporated herein by reference.

Each person's response to neural stimulation differs. In the case of retinal stimulation, a person's response varies from one region of the retina to another. In general, the retina is more sensitive closer to the fovea. Any stimulation, with magnitude less than the threshold of perception, is ineffective. Stimulation beyond a maximum level will be painful and possibly dangerous to the patient. It is therefore, important to map any video image to a range between the minimum and maximum for each individual electrode. With a simple retinal prosthesis, it is possible to adjust the stimulation manually by stimulating and questioning the patient. As resolution increases, it is tedious or impossible to adjust each electrode by stimulating and eliciting a patient response.

A manual method of fitting or adjusting the stimulation levels of an auditory prosthesis is described in U.S. Pat. No. 4,577,642, Hochmair et al. Hochmair adjusts the auditory prosthesis by having a user compare a received signal with a visual representation of that signal.

A more automated system of adjusting an auditory prosthesis using middle ear reflex and evoked potentials is described in U.S. Pat. No. 6,157,861, Faltys et al. An alternate method of adjusting an auditory prosthesis using the stapedius muscle is described in U.S. Pat. No. 6,205,360, Carter et al. A third alternative using myogenic evoked response is disclosed in U.S. Pat. No. 6,415,185, Maltan.

U.S. Pat. No. 6,208,894, Schulman describes a network of neural stimulators and recorders implanted throughout the body communicating wirelessly with a central control unit. U.S. Pat. No. 6,522,928, Whitehurst, describes an improvement on the system described in Schulman using function electro stimulation also know as adaptive delta modulation to communicate between the implanted devices and the central control unit.

The greatest dynamic range is achieved by setting the minimum stimulation at the threshold of perception and the maximum stimulation level approaching the pain threshold. It is unpleasant for a patient to first concentrate to detect the minimum perception and then be subjected to stimulation near the threshold of pain.

The human retina includes about four million individual photoreceptors. An effective visual prosthesis may include thousands of electrodes. An automated system is needed to adjust individual electrodes in a visual prosthesis for maximum benefit without the need for patient interaction in a long and difficult process.

SUMMARY OF THE INVENTION

The invention is a method of automatically adjusting an electrode array to the neural characteristics of an individual patient. The response to electrical neural stimulation varies from patient to patient and the relationship between current and perceived brightness is often non-linear. It is necessary to determine this relationship to fit the prosthesis settings for each patient. It is advantageous to map the perceptual responses to stimuli. The method of mapping of the present invention is to provide a plurality of stimuli that vary in current, voltage, pulse duration, frequency, or some other dimension; measuring and recording the perceptual response to those stimuli; deriving a formula or equation describing the map from the individual points; storing the formula; and using that formula to map future stimulation.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
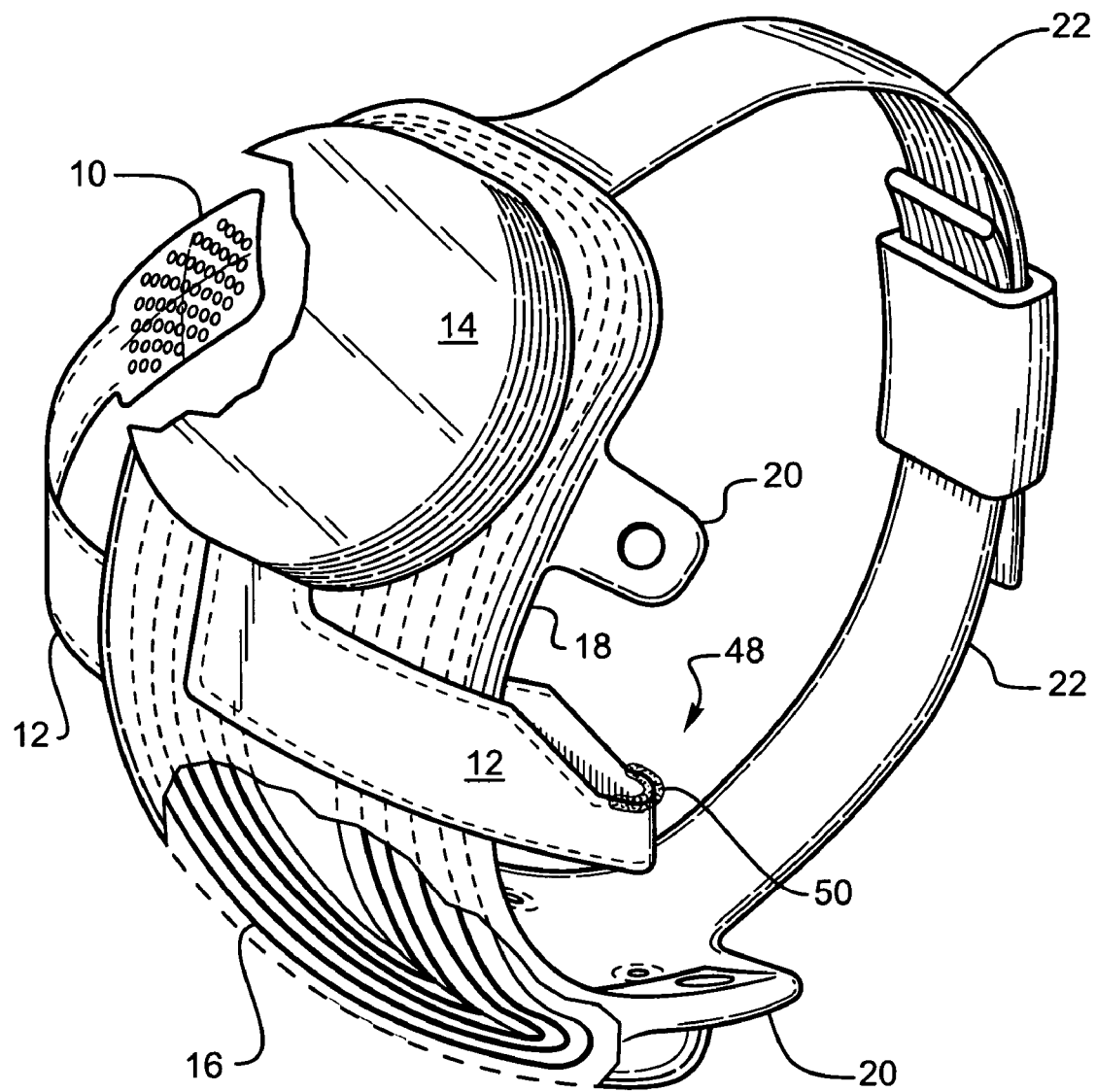
FIG. 1 is a perspective view of the implanted portion of the preferred retinal prosthesis.
Figure 2A:
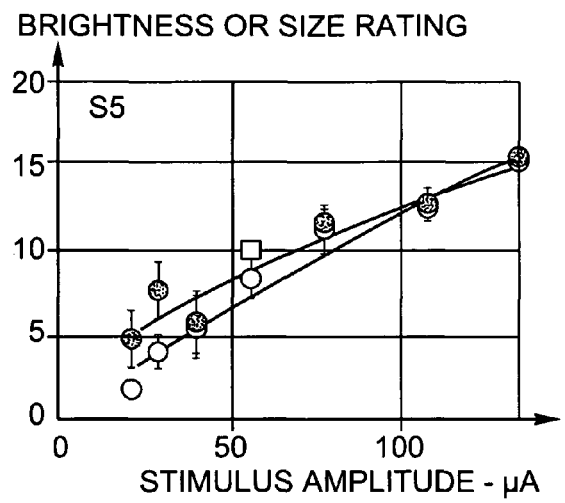
FIG. 2a-d are graphs showing typical current vs. brightness response.
Figure 2B:
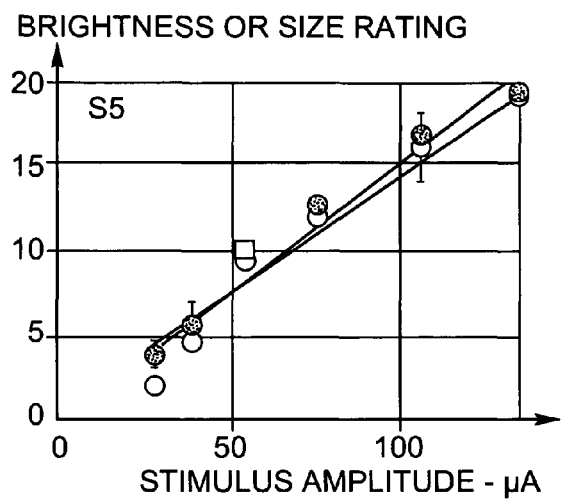
Figure 2C:
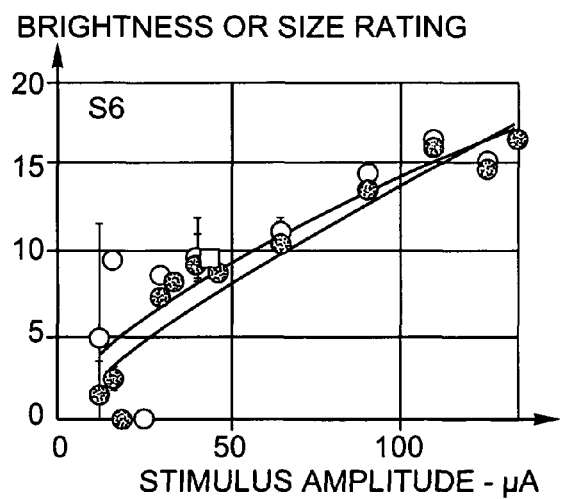
Figure 2D:
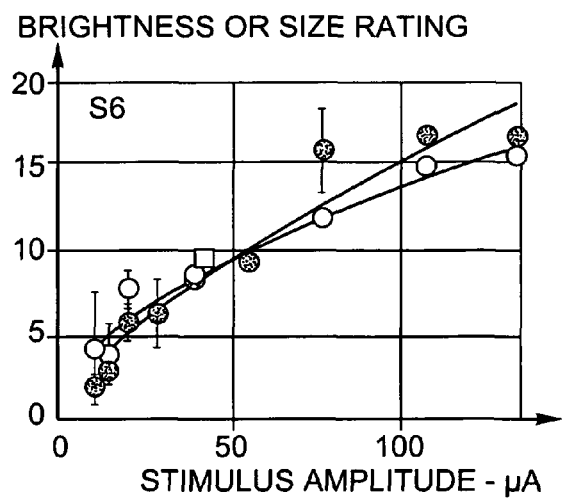

FIG. 1 shows a perspective view of the implanted portion of the preferred retinal prosthesis. A flexible circuit 1 includes a flexible circuit electrode array 10 which is mounted by a retinal tack (not shown) or similar means to the epiretinal surface. The flexible circuit electrode array 10 is electrically coupled by a flexible circuit cable 12, which pierces the sclera and is electrically coupled to an electronics package 14, external to the sclera.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The electronics package 14 and secondary inductive coil 16 are held together by a molded body 18. The molded body 18 may also include suture tabs 20. The molded body 18 narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap 22 can better support an oval shaped coil.

The preferred prosthesis includes an external portion (not shown) which includes a camera, video processing circuitry and an external coil for sending power and stimulation data to the implanted portion.

FIGS. 2a-d show typical perceptual responses collected from four patients. The perceptual responses differ in both the amplitude of the response curve and the shape of the response curve. All four patient perceptual responses, however, can be fitted by the function $B=aI^b$ where B is brightness, I is current amplitude, and a and b are parameters to be estimated from fitting the empirical data. Three data points will adequately define the function. Numerous statistical tools are available for automatically fitting the function to the three data points.

In this example the x axis represent the amplitude of stimulation using a single pulse. The y axis represents the patient's subjective rating of brightness where a stimulus rated as "10" is twice as bright as a stimulus rated as "5".

Figure 3:
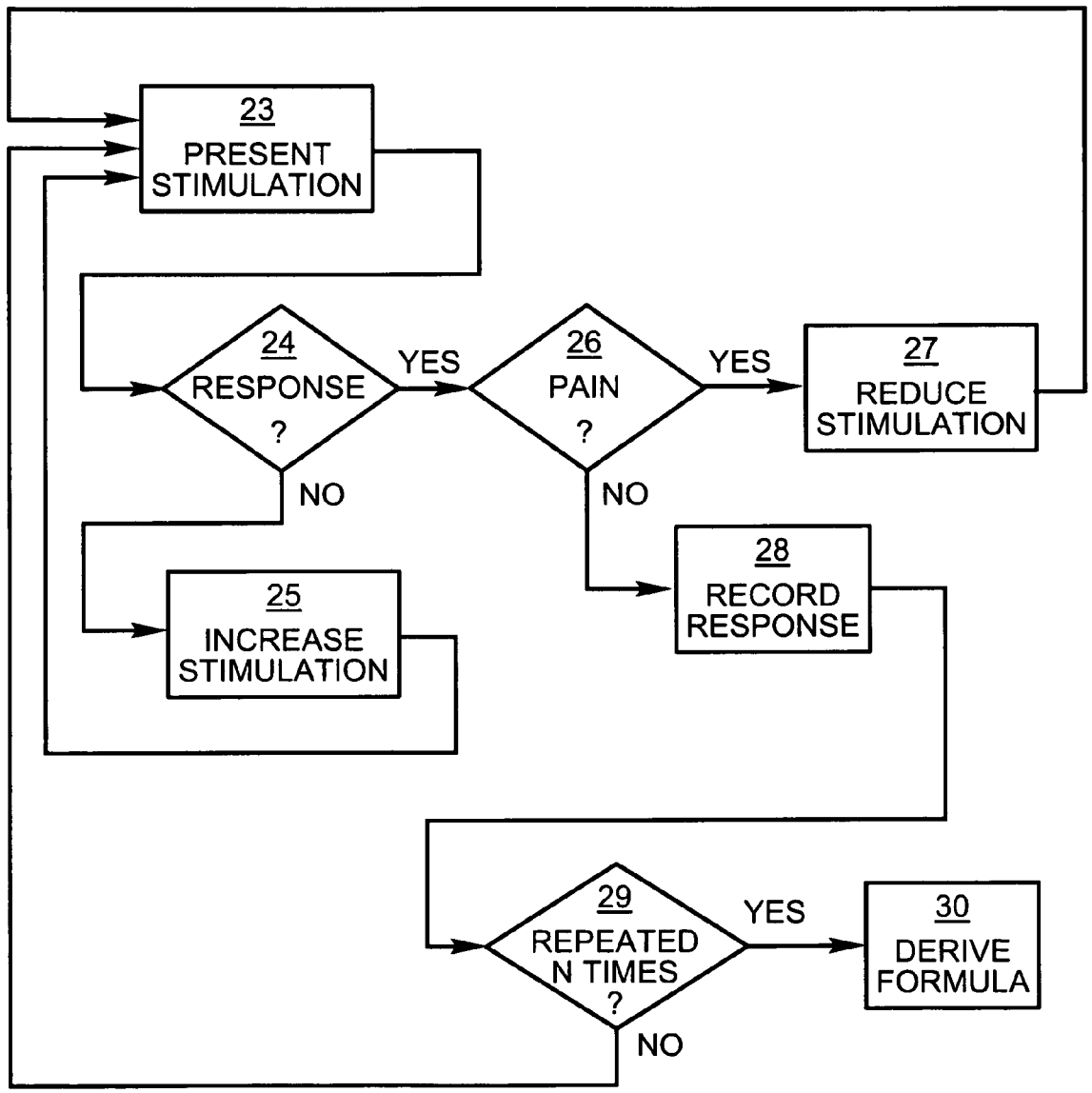
FIG. 3 is a flowchart show the brightness mapping method.

FIG. 3 shows a flow chart of the fitting procedure. In this case, we are using patient's ratings of subjective brightness but a measure of neural actively such a neural recording or pupil response (described below) could be used in an analogous fashion. First the fitting system must determine the perceptual brightness response to current relationship. This is accomplished by stimulating and measuring the subject reported brightness response rating at three points. It should be noted that the response is near linear in most cases. Hence, two points can be used to approximate the response, but three points will yield a more accurate fit. First, a stimulus is presented 23. If there is no response 24, the stimulus is increase 25 and stimulation is presented again 23. If there is a response to stimulus 24 and the response is pain 26, the stimulation is reduced 27 and stimulation is presented again 23. If there is a non-painful response it is recorded 28 in in non-volatile memory of the prosthesis device. Recording the response may include subjective response, neural recording or other physiological response. This process is repeated to get the required number of recorded responses, usually 3. If there are three recorded responses 29, an equation or formula is derived to describe the relationship between current and brightness relationship 30. The formula may be saved as an actual equation to be applied to the input value, or as a table of input and output values. It should also be noted that there must be a maximum charge limit sent in a visual prosthesis for safety reasons. Hence, the current variations must be limited by the preprogrammed maximum change. In the preferred embodiment, current is mapped to brightness. It should be noted that other a factors which may affect brightness, such as voltage, pulse width or frequency, may be mapped by the same method.

After the formula is established, input is received by the camera 31; the formula is applied to input data 32; and an output value is used to stimulate neural tissue 33.

Figure 4:
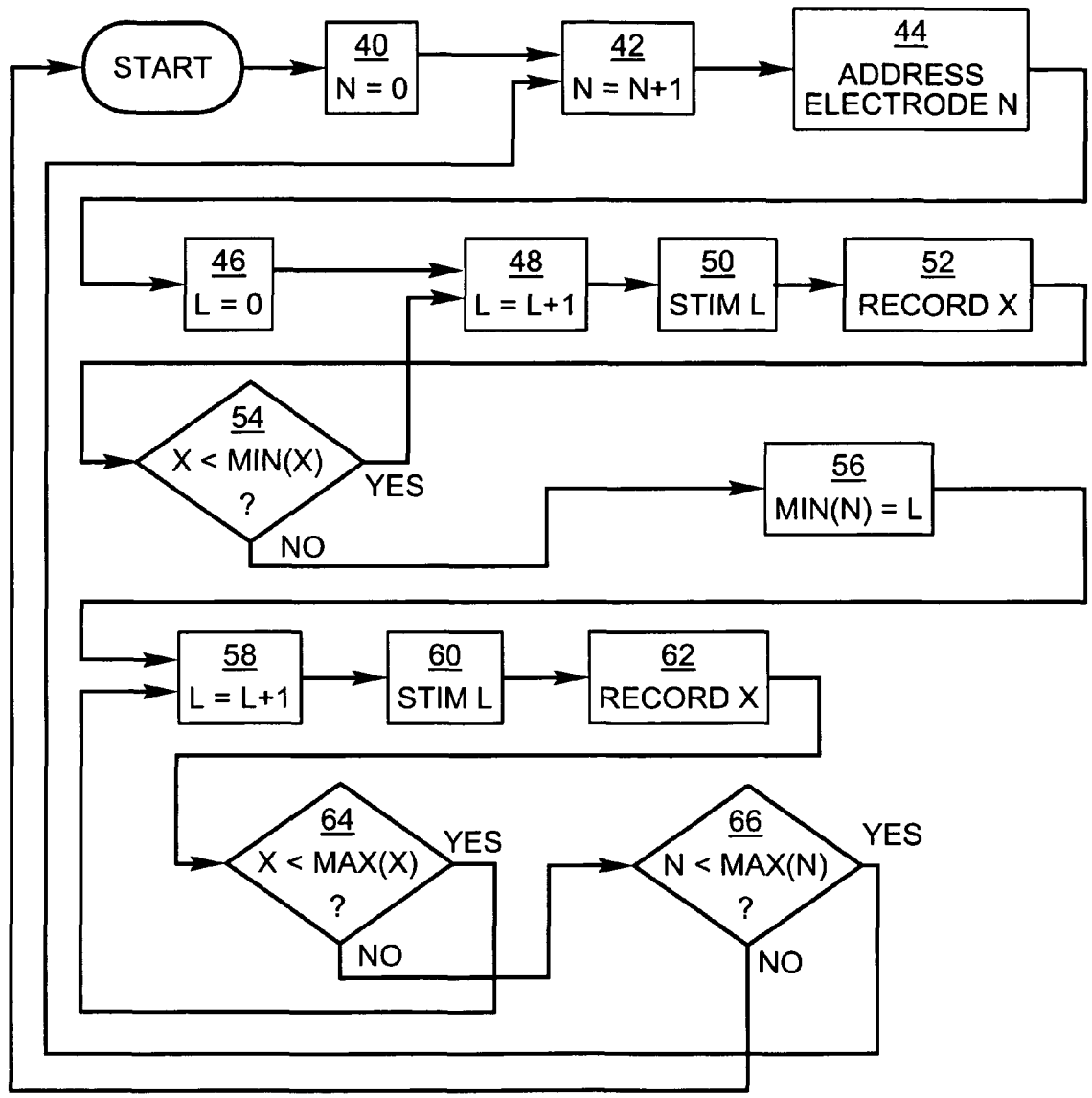
FIG. 4 is a flow chart showing an alternate process of auto fitting an electrode array.

FIG. 4 is a flow chart of an automatic fitting sequence which may be employed to gain the three points needed for the method described in FIG. 3, or may be used as an alternative fitting procedure. In the flow chart, the value N is the selected electrode, X is the neural activity recorded, and L is the level of stimulation (current amplitude. First N is set to 0 40 and then incremented 42. The first electrode, electrode N, is addressed 44. The stimulation level is set to zero 46, and then incremented 48. The neural tissue is stimulated at the minimum level 50. The stimulation is immediately followed by a recording of activity in the neural tissue 52. Alternatively, recording can be done simultaneously by an adjacent electrode. If recording is done simultaneously, one must distinguish between neural activity and electrical charge from the stimulating electrode. The neural response follows stimulation (see FIG. 6). Simultaneous stimulation and recording requires that the recording phase be longer than the stimulation phase. If so, the stimulation and neural response can be separated digitally. If the recorded neural activity is less than a predetermined level 54, the stimulation level is increased and steps 48-54 are repeated.

In most cases, the preset minimum level is any measurable neural activity. However, perception by the patient is the determining factor. If neural activity is detected and the patient reports no perception, the minimum level must be set higher. Once minimum neural activity is recorded, the stimulation level is saved in memory 56. The level is then further increased 58 and stimulation is repeated 60. Again stimulation is immediately followed by recording neural activity 62. If a predetermined maximum level has not been reached, steps 58-64 are repeated until the predetermined maximum stimulation level is obtained. Once the predetermined maximum stimulation level is obtained, steps 42-64 are repeated for the next electrode. The process is continued until a minimum and maximum stimulation level is determined for each electrode 66.

To obtain the subjective brightness or neural response for the necessary three points, one first finds the stimulus amplitude (the intensity of the stimulus can also be varied along other dimensions) which is barely detectable by the patient or provokes a minimally detectable neural response. One then presents the stimulus at that value (e.g. the amplitude value V=42) repeatedly until one has an accurate measurement of the subjective brightness or neural response at that stimulus intensity. One then finds the stimulus amplitude that is just under the safety limit or pain threshold, and measures the apparent brightness or neural response at that stimulus intensity. Finally one finds apparent brightness or neural response for a stimulus whose amplitude is halfway (or intermediate) between those two points. If additional data points are desired, equal distant points such as 25% and 75% should be used.

The range of intensities used for stimulation during operation of the device will fall within the range that is measured during the fitting procedure. Very low or high intensity values may not be used in normal function/.

The maximum stimulation level borders on discomfort for the patient. Because the automatic fitting process is automated, high levels of stimulation are only applied for a few microseconds. This significantly decreases the level of discomfort for the patient compared with stimulating long enough to elicit a response from the patient.

The fitting process is described above as an incremental process. The fitting process may be expedited by more efficient patterns. For example changes may be made in large steps if it the detected response is significantly below the desired response, followed by increasingly small steps as the desired response draws near. The system can jump above and below the desired response dividing the change by half with each step.

Often, neural response in a retina is based, in part, on geographical closeness. That is, neurons closer to the fovea require less stimulation than neurons farther from the fovea. Hence once a stimulation is level is set for an electrode, one can presume that the level will be similar for an adjacent electrode. The fitting process may be expedited by starting at a level near the level set for a previously fit adjacent electrode.

Automating the fitting process has many advantages. It greatly expedites the process reducing the efforts of the patient and clinician. Further, the automated process based on measured neural responses is objective. Patient perceptual responses are subjective and may change over time due to fatigue. In some cases, a patent may not be able to provide the required responses due to age, disposition, and/or limited metal ability.

Figure 5:
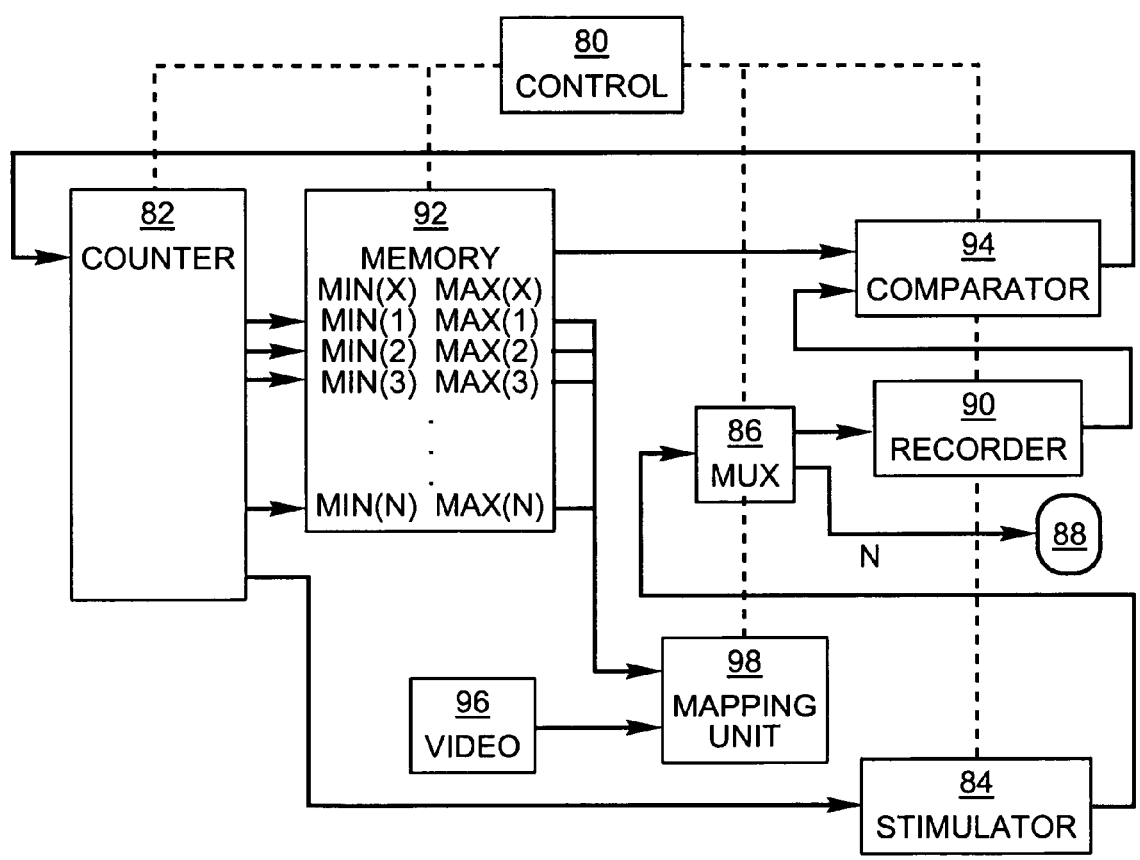
FIG. 5 depicts a block diagram of the retinal prosthesis electronic control unit.

FIG. 5 depicts a block diagram of the control unit. The block diagram is a functional diagram. Many of the functional units would be implemented in a microprocessor. A control unit 80 sets and increments a counter 82 to control the stimulation level of the stimulator 84. The stimulation signal is multiplexed in MUX 86 to address individual electrodes 88. After each stimulation, the addressed electrode returns a neural activity signal to a recorder 90. The signal is compared to the stored minimum or maximum level (stored in a memory 92) in a comparator 94. After programming, a signal from a video source 96, or other neural stimulation source, is adjusted in a mapping unit 98, in accordance with the minimum and maximum levels stored in the memory 92. The adjusted signal is sent to the stimulator 84, which in synchronization with MUX 86 applies the signal to the electrodes 88. The electronics for the control unit could be external or within the implanted prosthesis.

Figure 6:
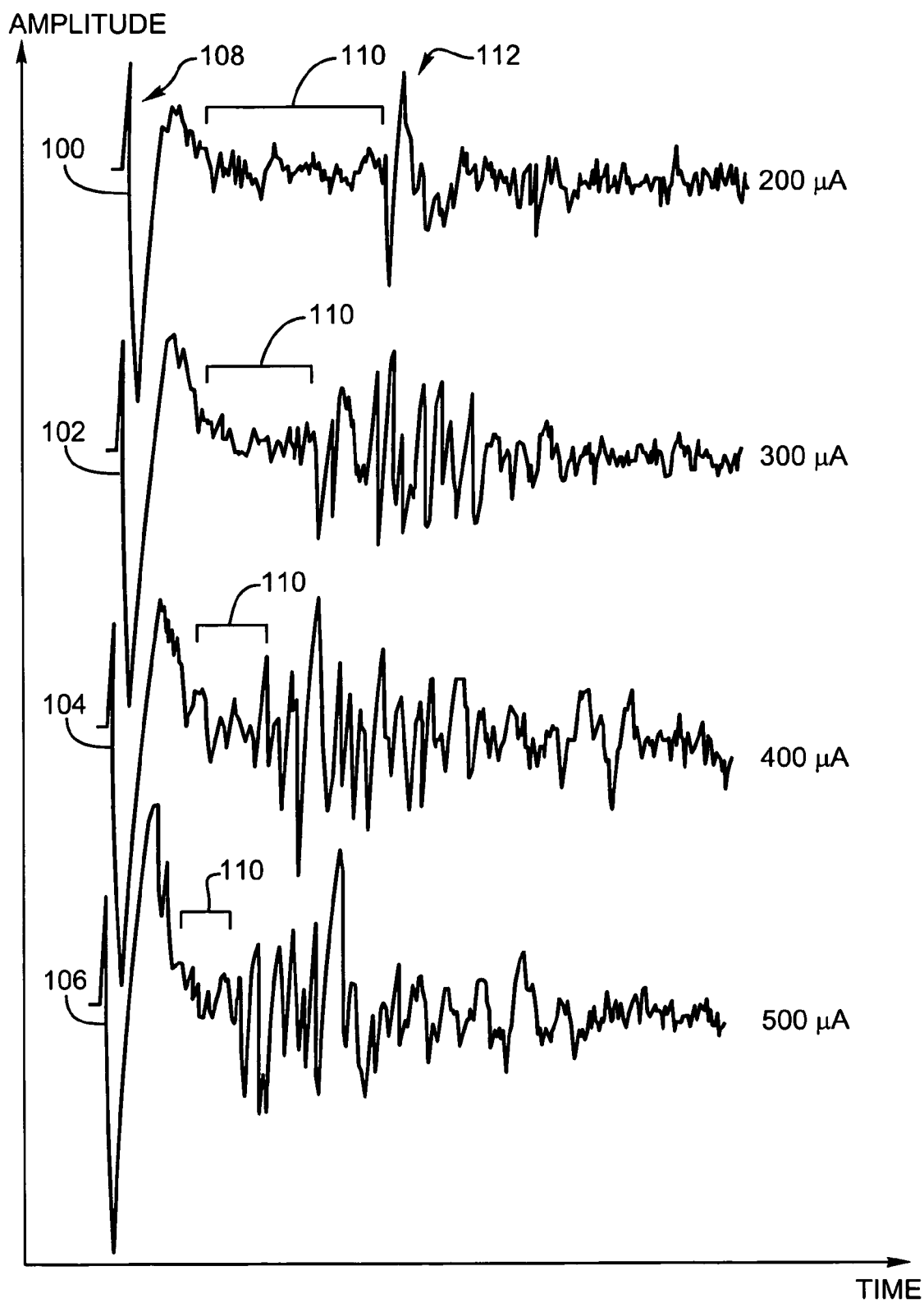
FIG. 6 is a graph depicting a typical neural response to electrical input.

FIG. 6 is a graphical representation of the neural response to electrical stimulus. This figure is derived from actual recordings of a frog retina. Response in a human retina will be similar and can be measured by a retinal electrode, implanted cortical electrode, or external cortical electrode commonly known as a visual evoked response or VEP. The vertical axis is current while the horizontal axis is time. Four curves 100-106 show the response at varying input current levels. An input pulse 108, is followed by a brief delay 110, and a neural response 112. Hence, it is important to properly time the detecting function. Either the stimulating electrode must be switched to a detecting electrode during the brief delay or detecting must occur on another electrode and continue long enough to record the neural response. It should also be noted that the delay period 110 becomes shorter with increased stimulation current. Hence, the system must switch faster from stimulation mode to detecting mode with increased current. The change in delay time may also be used as an additional indication of neural response. That is, the minimum and maximum may be determined by matching predetermined delay times rather than predetermined output levels. As stimulation increases, it becomes more useful to employ an alternate recording means as described in the following alternate embodiments.

In a first alternate embodiment, the recording electrode may be cortical electrode mounted on or near the visual cortex. Temporary external electrodes placed on the scalp proximate to the visual cortex may record neural activity in the visual cortex. This allows the system to account for any variations in neural processing between the retina and the visual cortex. It, however, requires electrodes either implanted in the visual cortex or placed temporarily near the visual cortex. This alternate embodiment may be combined with the preferred embodiment by first using cortical electrodes to perform an initial fitting of the prosthesis in a clinic. Thereafter, retinal recording may be used to readjust the prosthesis for any changes over time.

Figure 7:
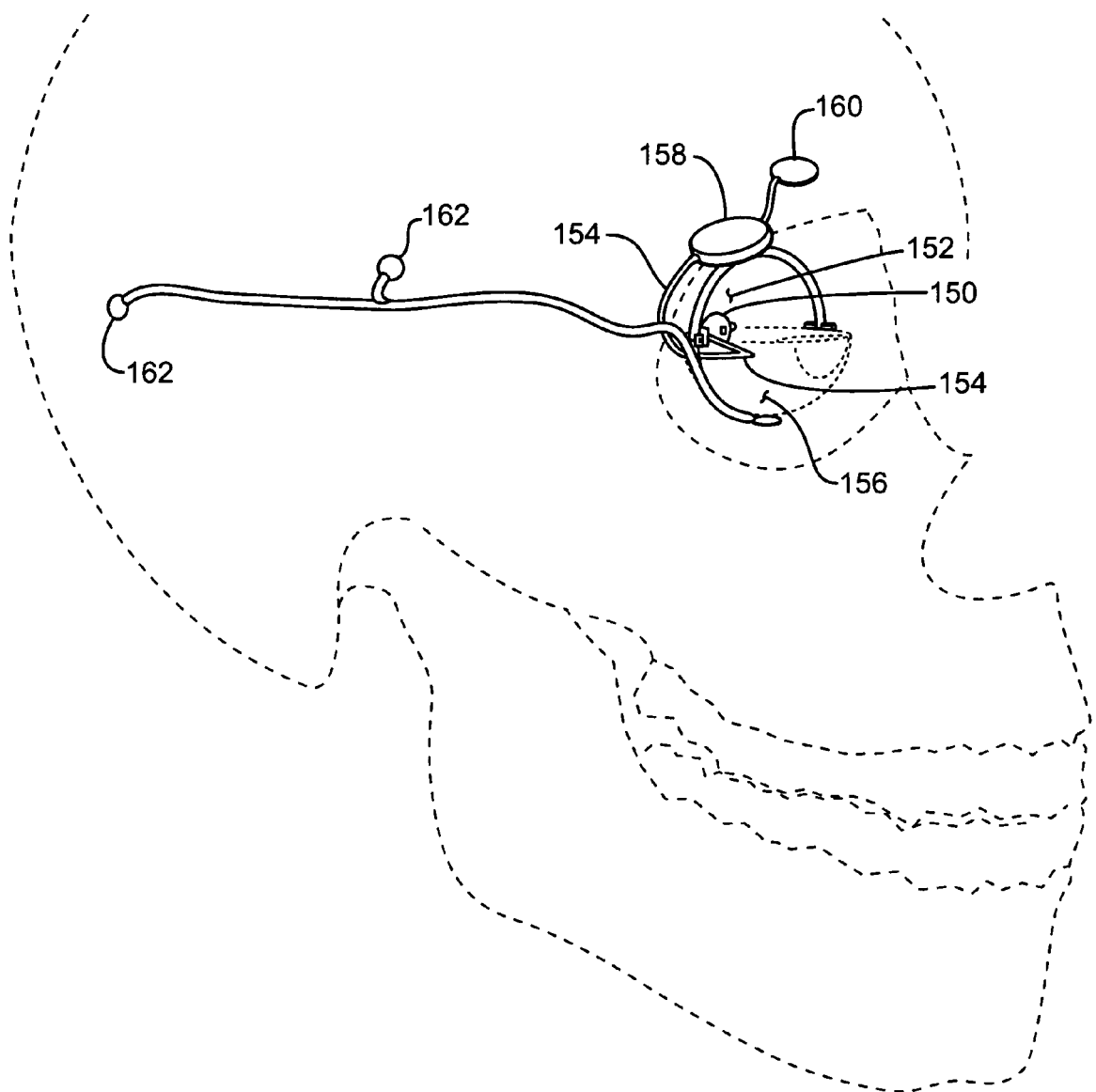
FIG. 7 depicts an alternate fitting process using cortical recording.

FIG. 7 shows the first alternate retinal prosthesis. A stimulating electrode array 150 is placed against the outer surface of a retina 152 (epiretinally). A cable 154 pierces a sclera 156 and attaches to an electronic control unit 158. A return electrode 160 may be placed distant from the retina 152. The stimulating electrode array 150 is a plurality of tiny electrodes. One or more recording electrodes 162 are placed in near the visual cortex. The recording electrodes may be temporary external electrodes, implanted electrodes under the scalp, or electrode implanted within the visual cortex.

In a second alternate embodiment, the recording electrode may be either implanted in the iris, or placed externally near the iris. The iris contracts when increasing light levels enter the eye. Electrical stimulation of the retina also causes the iris to contract, because the body perceives an increase in light entering the eye. Conversely, the iris expands in response to a decrease in electrical stimulation. While the response of the iris is relatively slow, the neurological signals initiating a change in the iris respond quickly. Measuring these signals may provide alternate feed back as to the body's response to the electrical stimulus. Alternatively, an optical device aimed at the eye may detect the diameter of the iris.

Figure 8:
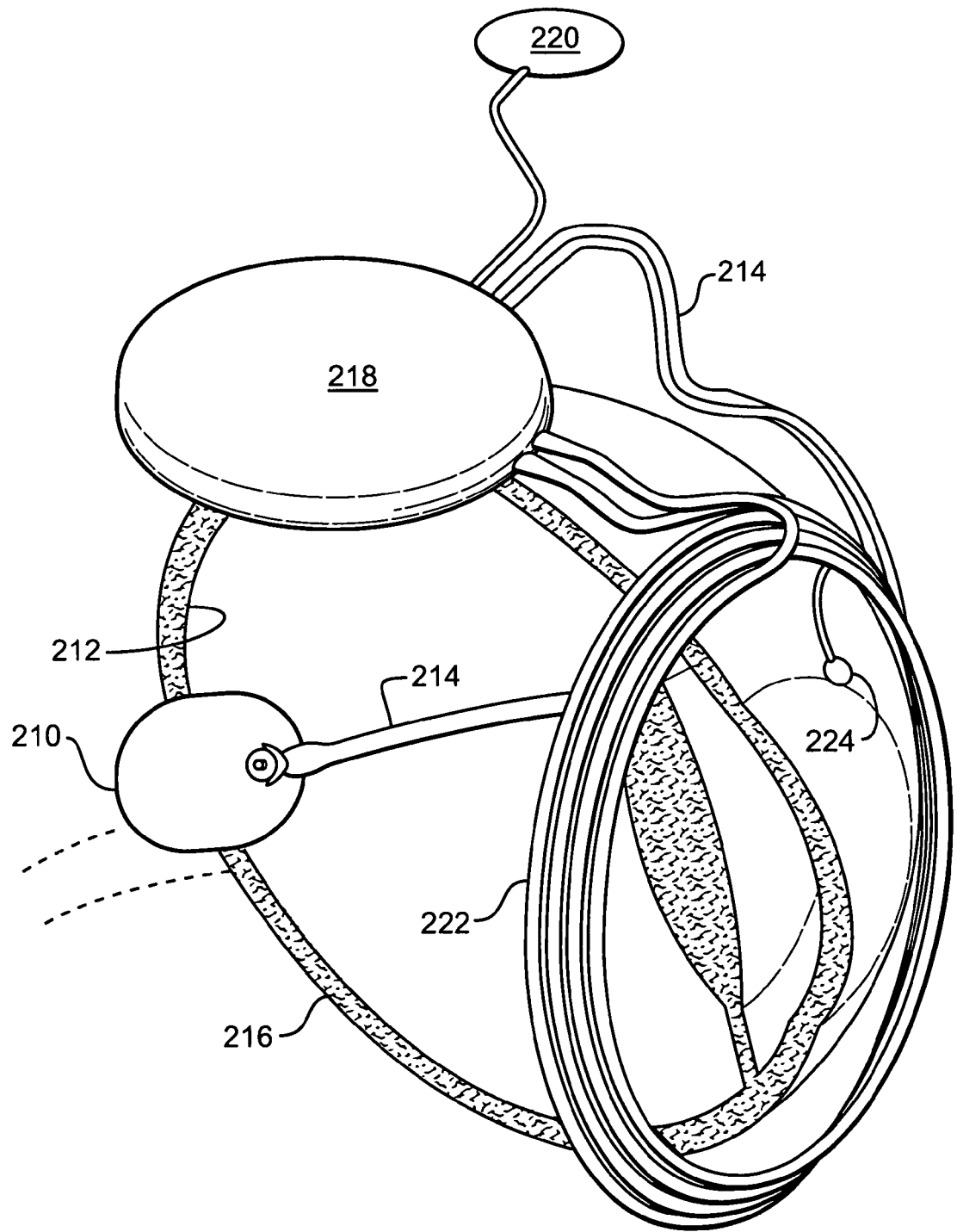
FIG. 8 depicts an alternate fitting process using iris recording.

FIG. 8 shows the second alternate retinal prosthesis. A stimulating electrode array 210 is placed against the outer surface of a retina 212 (epiretinally). A cable 214 pierces a sclera 216 and attaches to an electronic control unit 218. A return electrode 220 may be placed distant from the retina 212. The stimulating electrode array 210 is a plurality of tiny electrodes. A recording electrode 224 is place in the periphery of the iris sensing electrical stimulus to the iris.

In a third alternate device, electroluminescent pigments may be applied to the retina. Electroluminescent pigments cause an individual cell to glow when it fires an action potential. A camera of the type used for retinal photos may detect neural response by detecting the electroluminescent glow of the applied pigment.

Accordingly, what has been shown is an improved method of stimulating neural tissue for improved response to brightness. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

The invention claimed is:

1. A method of fitting a visual prosthesis, comprising:
    applying a plurality of stimuli to visual neural tissue;
    measuring brightness responses to said stimuli to determine a threshold of perception;
    applying an additional stimuli higher than said threshold of perception:
    measuring a brightness response to said additional stimuli;
    deriving a formula comprising a stimulation curve estimating brightness levels not tested,
    said formula being derived starting from empirical data of said threshold of perception and said brightness response to said additional stimuli and corresponding to a curve fitting of the empirical data; and
    generating said stimuli by applying said formula to visual input.

2. The method according to claim 1, wherein said stimuli vary according to applied current.

3. The method according to claim 1, wherein said stimuli vary according to applied voltage.

4. The method according to claim 1, wherein said stimuli vary according to applied frequency.

5. The method according to claim 1, wherein said stimuli vary according to applied pulse width.

6. The method according to claim 1, wherein said brightness responses are perceptions of brightness reported by a user.

7. The method according to claim 1, wherein said responses are neural responses recorded from the visual neural tissue of the user.

8. The method according to claim 1, wherein said responses are recorded physiological changes in the iris of a user.

9. The method according to claim 1, wherein said responses are recorded neural activity of the user.

10. The method according to claim 1, further comprising creating a table based on said formula.

11. The method according to claim 10, wherein said step of generating stimuli by applying said formula comprises applying values from said table.

12. The method according to claim 1, wherein said formula defines brightness as slope times current to the power of shape where slope and shape are derived terms.

13. The method according to claim 1, wherein said formula defines brightness as slope times current plus threshold, where slope and threshold are derived terms.

14. The method according to claim 1, wherein said formula is a function $$B = a\,I^b,$$

wherein B represents brightness, I represents current amplitude, and a and b represent parameters estimated from fitting the empirical data.

15. A visual prosthesis, comprising:
- an array of electrodes suitable to be placed in proximity to visual neural tissue;
- a camera for receiving a visual scene; and
- a control device coupling said camera to said array of electrodes including a neural stimulator for applying a plurality of stimuli to visual neural tissue;
- means for measuring brightness responses to said stimuli for determining a threshold of perception;
- means for applying an additional stimuli higher than said threshold of perception;
- means for measuring a brightness response to said additional stimuli;
- means for deriving a formula comprising a stimulation curve estimating brightness levels not tested, said formula being derived starting from empirical data of said threshold of perception and said brightness response to said additional stimuli and corresponding to a curve fitting of the empirical data; and
- means for generating stimuli by applying said formula to visual input from said camera.

16. The visual prosthesis according to claim 15, wherein said means for measuring brightness responses is a means for measuring neural activity in the retina.

17. The visual prosthesis according to claim 15, wherein said means for measuring brightness responses is a means for measuring neural activity in the visual cortex.

18. The visual prosthesis according to claim 15, wherein said means for measuring brightness responses is a means for measuring a patient's reported responses.

19. The visual prosthesis according to claim 15, wherein said means for measuring brightness responses is a means for measuring movement of the iris.

20. The visual prosthesis according to claim 15, wherein said means for generating stimuli varies by applied current.

21. The visual prosthesis according to claim 15, wherein said means for generating stimuli varies by applied voltage.

22. The visual prosthesis according to claim 15, wherein said means for generating stimuli varies by applied frequency.

23. The visual prosthesis according to claim 15, wherein said means for generating stimuli varies by applied pulse duration.

24. The visual prosthesis according to claim 15, wherein said formula is a function $$B = a\,I^b,$$

wherein B represents brightness, I represents current amplitude, and a and b represent parameters estimated from fitting the empirical data.

* * * * *